United States Patent [19]

Chan

[11] 4,140,791

[45] Feb. 20, 1979

[54] 1,4-DI-(2,6-DIMETHYLPHENYL)-2,5-PIPERAZINEDIONE AND ITS FUNGICIDAL USE

[75] Inventor: David C. K. Chan, Petaluma, Calif.

[73] Assignee: Chevron Research Company, San Francisco, Calif.

[21] Appl. No.: 910,982

[22] Filed: May 30, 1978

[51] Int. Cl.$^2$ .................... A01N 9/22; C07D 241/08
[52] U.S. Cl. ................................ 424/250; 544/385
[58] Field of Search ..................... 424/250; 544/385

[56] References Cited

U.S. PATENT DOCUMENTS

| | | | |
|---|---|---|---|
| 3,239,528 | 3/1966 | Von Bebenburg et al. | 544/385 |
| 3,673,172 | 6/1972 | Svokos et al. | 544/385 |
| 3,692,908 | 9/1972 | Tetenbaum et al. | 544/385 |

OTHER PUBLICATIONS

Hall, Jr.; J. Am. Chem. Soc., 80 6404 (1958).
Irikura et al; C. A. vol. 78 (1973) 124631m.
C. A. vol. 54 (1960) 4596e.

*Primary Examiner*—Allen J. Robinson
*Attorney, Agent, or Firm*—Dix A. Newell; T. G. DeJonghe

[57] ABSTRACT

1,4-Di-(2,6-dimethylphenyl)-2,5-piperazinedione has been found to be highly effective for the control of late blight, downy mildew and Phytophthora crown and root rot fungal diseases.

8 Claims, No Drawings

1,4-DI-(2,6-DIMETHYLPHENYL)-2,5-PIPERA-ZINEDIONE AND ITS FUNGICIDAL USE

DESCRIPTION OF THE PRIOR ART

P. W. Abenius, Chem. Ber. 21 1665 (1888) discloses the preparation of several 1,4-diaryl-2,5-piperazinediones (N,N'-diaryldiketopiperazines). H. K. Hall, Jr., J. Am. Chem. Soc., 80 6404 (1958) describes polymerization studies of 1,4-dimethyl-2,5-piperazinedione and 1,4-piperazindeione. Chem. Abs. 78 124631m (1973) discloses the use of 1,4-diaryl-2,5-diketopiperazines as antigastric ulcer agents. Chem. Abs. 54 4596e (1959) describes the electrolytic reduction of 1,4-disubstituted-2,5-diketopiperazines.

DESCRIPTION OF THE INVENTION 1,4-Di-(2,6-dimethylphenyl)-2,5-piperazinedione is a novel compound which can be prepared by the dimerization of 2,6-dimethyl-alpha-chloroacetanilide. It has now been found that this compound is highly effective for the control of late blight diseases caused by *Phytophthora infestans*, downy mildew diseases caused by fungal species of the *Peronosporaceae* family and plant crown and root rots caused by fungal species of the *Phytophthora* genus.

Late blight caused by the fungus *Phytophthora infestans* is a common and wide-spread disease of tomatoes and potatoes.

Downy mildew is a widely distributed group of diseases of plants grown in the cool, humid areas of the world. Downy mildew diseases include downy mildew of lettuce caused by the species *Bremia lactucae*; downy mildew of spinach caused by the species *Peronospora effusa*; down mildew of onions caused by the species *P. destructor*; downy mildew of soybeans caused by the species *P. manshurica urica*; downy mildew of broccoli caused by the species *P. parasitica*; downy mildew of cabbage caused by the species *P. parasitica ssp. brassicae*; downy mildew of tobacco caused by the species *P. tabacina*, downy mildew of alfalfa caused by the species *P. trifoliorum*; downy mildew of sugar beets caused by the species *P. schactii*; downy mildew of lima beans caused by the species *Phytophthora phaseoli*; downy mildew grapevines caused by the species *Plasmopara viticola*; downy mildew of watermelon, cucumber, squash and related plants caused by the species *Pseudoperonospora cubensis*; and downy mildew of hops caused by the species *Pseudoplasmopara humuli*.

Phytophthora fungi cause a variety of crown and root rot diseases in plants.

*Phyophthora* species causing crown and root rot disease in plants include *Phytophthora cactorum* (crown rot of walnut, root rot of sweetcloves, root cankers of avocado trees, *Phytophthora* rot of apples and pears); *P. cambivora* (ink disease of citrus trees); *P. capsici* (root rot of peppers; *P. cinnamoni* (heart and root rot of pineapples, *Phytophthora* root rot of avocados, root rot of citrus trees); *P. citricola* (brown rot gummosis); *P. citrophthora* (root rot of citrus trees); *P. cryptogea* (crown and root rot of tomato, safflower and tobacco); *P. dreschleri* (root rot of safflower); *P. erythrosytica* (pink rot of potato); *P. fragariae* (red stele of strawberry); *P. megosperma* (root rots of cherry, peach and walnuts); *P. nicotianae* (tobacco black shank); *P. palmivora* (root rot of citrus trees, bud rot of coconut palm, black pod rot of cacao); *P. parasitica* root rot of watermelons, root rot of citrus trees); and *P. syringae* (root rot of citrus).

The compound of this invention is particularly useful as a fungicide because it cures established fungal infections. This permits economical use of the fungicide of the invention, because it need not be applied to plants unless fungal infection actually occurs. Thus, a preventive program of applying the fungicide against potential fungal infection is not necessary.

The compound of the invention is applied in fungicidally effective amounts to fungi and/or their habitats, such as vegetative plant hosts and their growth medium or environment. The amount used will, of course, depend on several factors such as the host and the species of fungus. The compound of the invention is generally incorporated with conventional, biologically inert extenders or carriers normally employed for facilitating dispersion of the active fungicidal ingredient, recognizing that the formulation and mode of application may effect the activity of the fungicide. Thus, the compound of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols and polyvinyl alcohols, polyethylene oxides, sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal compositions.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other non-volatile organic solvents. For application, these concentrates are dispersed in water or other liquid carrier and are normally applied as a spray to the area to be treated.

Other useful formulations for fungicidal applications include simple solutions of the active compound in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredients is dispersed in finely divided form as a result of vaporization of a low-boiling dispersent solvent carrier, such as fluorinated hydrocarbons, may also be used. All of those techniques for formulating and applying fungicides are well known in the art.

The percentages by weight of the active fungicide may vary according to the manner in which the composition is to be applied and the particular type of formulation, but in general comprise 0.5 to 95% of the active fungicide by weight of the fungicidal composition.

The fungicidal compositions may be formulated and applied with other active ingredients, including other fungicides, insecticides, nematocides, bactericides, plant growth regulators, fertilizers, etc.

EXAMPLES

Example 1 — Preparation of 1,4-di-(2,6-dimethylphenyl)-2,5-piperazinedione

A round-bottom flask was purged with nitrogen and filled with 161 g (0.81 mol) 2,6-dimethyl-alpha-chloroacetanilide and 700 ml dimethoxyethane. The flask was immersed in an ice bath. 32.9 g (0.81 mol) of sodium hydride (50% dispersion in mineral oil) was then added in small portions to the flask over a 1-hour period. The ice bath was removed and the reaction mixture was stirred at about 25° C. for 16 hours. The reaction mixture was filtered to give the product as white crystals. The mother liquor was evaporated under reduced pressure to give additional white crystalline product. The solid products were washed with water, combined, washed with 200 ml ethyl ether, and dried in a vacuum oven. The total yield of product, m.p. 233–235° C., was 109 g (83.4%). Elemental analysis for $C_{20}H_{22}N_2O_2$ showed:

| | Calc. | Found |
|---|---|---|
| %C | 74.5 | 73.8 |
| %H | 6.9 | 6.8 |
| %N | 8.7 | 8.9 |

Example 2 — Tomato Late Blight Control

The compound of the invention was tested for the control of the Tomato Late Blight organism *Phytophthora infestans.* For comparison, several closely related compounds were also tested. Five- to six-week-old tomato (cultivar Bonny Best) seedlings were used. The tomato plants were sprayed with a 250-ppm solution of the test compound in acetone, water and a small amount of a non-ionic emulsifier. The sprayed plants were then inoculated one day later with the organism, placed in an environmental chamber and incubated at 66–68° F. and 100% relative humidity for at least 16 hours. Following the incubation, the plants were maintained in a greenhouse at 60–80% relative humidity for approximately 7 days. The percent disease control provided by a given test compound was based on the percent disease reduction relative to untreated check plants. The compounds found to be effective at the test concentration and the results are tabulated in Table I.

TABLE I

Tomato Late Blight Control with Compounds of the Formula:

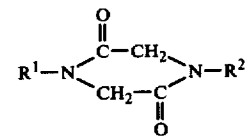

| No. | $R^1$ | $R^2$ | % Control |
|---|---|---|---|
| 1 | 2,6-$(CH_3)_2$-$\phi$ | 2,6-$(CH_3)_2$-$\phi$ | 93 |
| 2 | $\phi$ | $\phi$ | 0 |
| 3 | 2,5-$(C_2H_5)\phi$ | 2,6-$(C_2H_5)\phi$ | 0 |
| 4 | 2-$(iC_3H_7)2\phi$ | 2-$(iC_3H_7)_2\phi$ | 35 |
| 5 | $CH_3$ | 2,6-$(CH_3)_2$-$\phi$ | 0 |
| 6 | 2-Cl-6-$CH_3$-$\phi$ | 2-Cl-6-$CH_3$-$\phi$ | 0 |
| 7 | 4-Cl-$\phi$ | 4-Cl-$\phi$ | 0 |
| 8 | 2,6-$(CH_3)_2$-$\phi$ | $\phi$ | 0 |
| 9 | 3,4-$(CH_3)_2$-$\phi$ | 3,4-$(CH_3)_2$-$\phi$ | 0 |
| 10 | 2,6-$(CH_3)_2$-$\phi$ | H | 0 |
| 11 | 2,3,6-$(CH_3)_3$-$\phi$ | 2,3,6-$(CH_3)_3$-$\phi$ | 0 |
| 12 | 2,6-$(CH_3)_2$-$\phi$ | 3,6-$Cl_2$-$\phi$ | 0 |
| 13 | 2,6-$(CH_3)_2$-$\phi$ | 2-$C_2H_5$-$\phi$ | 0 |
| 14 | 2-$CH_3$-6-$C_2H_5\phi$ | 2-$CH_3$-6-$C_2H_5\phi$ | 0 |
| 15 | 2,6-$(CH_3)_2$-$\phi$ | 2-$CH_3$-$\phi$ | 0 |
| 16 | 2,6-$(CH_3)_2$-$\phi$ | 2-$CH_3$-6-$C_2H_5\phi$ | 0 |
| 17 | 2,6-$(CH_3)_2$-$\phi$ | 2-Cl-6-$CH_3$-$\phi$ | 0 |
| 18 | 2-$CH_3$-$\phi$ | 2-$CH_3$-$\phi$ | 0 |
| 19 | $CH_2$-$\phi$ | $CH_2$-$\phi$ | 56 |
| 20 | $CH_3$ | $CH_3$ | 73 |

$\phi$ represents phenyl

Example 3 — Eradicant Tomato Late Blight Control

The compound of the invention was tested for the eradicant control of the Tomato Late Blight organism *Phytophthora infestans.* Five- to six-week-old tomato (cultivar Bonny Best) plants were used. The tomato plants were inoculated with the organism, placed in an environmental chamber and incubated at 18–22° C. and 100% relative humidity for 2 days. The plants were then sprayed with a 100-ppm solution of the test compound in acetone, water and a small amount of a non-ionic emulsifier. The sprayed plants were allowed to dry and then were maintained in a greenhouse at 18–22° C. and at 95–100% relative humidity. Seven days after inoculation, the plants were observed for fungal infections. The amount of disease control provided by the test compound was based on the amount of disease reduction relative to untreated check plants. The compound was found to give 96% disease control.

Example 4 — Preventive Grape Downy Mildew Control

A test was conducted to determine the effectiveness of the compound of the invention for the control of grape downy mildew (*Plasmopara viticola*). Detached leaves of 3-month-old Cabernet Sauvignon grape plants were used as hosts. Four leaves were used in each test. The leaves were sprayed with a solution of the test compound in a 1% acetone/99% water solution containing 40 ppm of a non-ionic surfactant. The sprayed leaves were dried and inoculated with 25 droplets of a sporangial suspension of the organism (400,000 conidia/milliliter water). After inoculation, the leaves were kept in a high-humidity chamber. After 10 days, the amount of disease control was determined. The percent disease control provided by the test compound was based on the percent disease reduction relative to untreated check leaves. The percent control was found to be 54%.

Example 5 — Eradicant Grape Downy Mildew Control

The compound of the invention was tested for the eradicant control of the grape downy mildew organism *Plasmopara viticola*. Detached leaves of between 70- and 85-mm diameter of 7-week-old *Vitis vinifera* cultivar Emperor grape seedlings were used as hosts. The leaves were inoculated with the organism and placed in an environment chamber and incubated at 18°-22° C.and at about 100% relative humidity for 2 days. The leaves were then sprayed with a 16-ppm solution of the test compound in acetone. The sprayed leaves were then maintained at 18-22° C. and at about 100% relative humdity. Seven to nine days after inoculation, the amount of disease control was determined. The percent disease control provided by the test compound was based on the percent disease reduction relative to non-treated check plants. The disease control was 100%.

Example 6 — Systemic Soil Drench Treatment for Safflower Crown and Root Rot Control The compound of the invention was tested to determine its systemic activity in soil-drench applications against the safflower crown and root rot organism *Phytophthora cryptogea*. Two-week-old safflower seedlings were used as hosts. Pots containing the seedlings were drenched with an aqueous suspension of the test compound at a test concentration of 100 ppm (four pots per concentration level). One day after treatment, a spawn of the organism was poured on the soil surface in the pots. The spawn was prepared by cultivating the organism in a mixture of oat flakes, potato dextrose and soil. The inoculated seedlings were then maintained in a greenhouse at 20-25° C.day and 15-20° C.night temperature. Three to four weeks after inoculation, the plant roots and crown were rated for disease. The percent disease control provided by the test compound was based on percent disease reduction relative to non-treated check plants. The disease control obtained was 90%.

Example 7 — Systemic Foliar Treatment for Safflower Crown and Root Rot Control The compound of the invention was tested to determine its systemic activity in foliar applications against the crown and root rot organism *Phytophthora cryptogea*. Two-week-old safflower seedlings wre used as hosts. Pots containing the seedlings were sprayed with an aqueous solution of the test compound at a test concentration of 100 pm. One day after treatment, a spawn of the organism was poured on the soil surface in the pots. The spawn was prepared by cultivating the organism in a mixture of oat flakes, potato dextrose and soil. The inoculated seedlings were then maintained in a greenhouse at 20-25° C.day and 15-20° C.night temperature. Three to four weeks after inoculation, the plant roots and crown were treated for disease. The percent disease control provided by the test compound was based on percent disease reduction relative to non-treated check plants. The percent disease control obtained was 89%.

What is claimed is:

1. 1,4-Di-(2,6-dimethylphenyl)-2,5-piperazinedione.

2. A method for controlling fungal infection in plants caused by *Peronosporaceae* fungi and *Phytophthora* fungi, which comprises applying to said fungi or their habitats a fungicidally effective amount of the compound of claim 1.

3. A method for controlling downy mildew fungal infection in plants caused by *Peronsporaceae* fungi which comprises applying to plants or plant hosts of *Peronsporaceae* fungi a fungicidally effective amount of the compound of claim 1.

4. A method for controlling downy mildew on grape plants which comprises applying to said grape plants a fungicidally effective amount of the compound of claim 1.

5. A method for controlling *Phytophthora* crown or root rot diseases which comprises applying to plants or plant hosts of Phytophthora fungi a fungicidally effective amount of the compound of claim 1.

6. A method for controlling fungal infection in plants caused by *Phytophthora infestans* which comprises applying to the plants or plant hosts of *Phytophthora infestans* a fungicidally effective amount of the compound of claim 1.

7. The method of claim 6 wherein the plants are potatoes and tomatoes.

8. A fungicial composition comprising a fungicidally effective amount of the compound of claim 1 and a biologically inert carrier.

* * * * *